United States Patent
Gomez et al.

(10) Patent No.: US 11,771,415 B2
(45) Date of Patent: Oct. 3, 2023

(54) SPECIALIZED KNOT PUSHER FOR SURGICAL PORT CLOSURE AND SUTURING DEVICES

(71) Applicant: New Wave Endo-Surgery Inc., Coconut Creek, FL (US)

(72) Inventors: Ricardo Alexander Gomez, Lighthouse, FL (US); Sandy Lawrence Heck, Los Angeles, CA (US); Juan Carlos Diaz, Pembroke Pines, FL (US); George Ferzli, Staten Island, NY (US)

(73) Assignee: New Wave Endo-Surgical Corp., Coconut Creek, FL (US)

( * ) Notice: Subject to any disclaimer, the term of this patent is extended or adjusted under 35 U.S.C. 154(b) by 20 days.

(21) Appl. No.: 16/839,370

(22) Filed: Apr. 3, 2020

(65) Prior Publication Data
US 2020/0315608 A1    Oct. 8, 2020

Related U.S. Application Data

(60) Provisional application No. 62/828,680, filed on Apr. 3, 2019.

(51) Int. Cl.
*A61B 17/04* (2006.01)
*A61B 17/00* (2006.01)

(52) U.S. Cl.
CPC ............ *A61B 17/0469* (2013.01); *A61B 2017/00477* (2013.01); *A61B 2017/0474* (2013.01)

(58) Field of Classification Search
CPC ........ A61B 17/0469; A61B 2017/0474; A61B 17/0057; A61B 2017/00663; A61B 2017/00477; A61B 2017/0046; A61B 17/0482; A61B 2017/047–0479
See application file for complete search history.

(56) References Cited

U.S. PATENT DOCUMENTS

| | | | | |
|---|---|---|---|---|
| 5,176,691 A * | 1/1993 | Pierce | ................ | A61B 17/0469 606/144 |
| 5,643,293 A * | 7/1997 | Kogasaka | .......... | A61B 17/0469 112/169 |
| 6,200,329 B1 * | 3/2001 | Fung | .................. | A61B 17/0487 606/232 |
| 2003/0055438 A1 * | 3/2003 | Hirata | .............. | A61B 17/12013 606/139 |
| 2014/0066953 A1 * | 3/2014 | Keating | ............. | A61B 17/3423 606/130 |

* cited by examiner

*Primary Examiner* — Sarah A Long
*Assistant Examiner* — Raihan R Khandker
(74) *Attorney, Agent, or Firm* — Grogan, Tuccillo & Vanderleeden, LLP

(57) ABSTRACT

A knot pusher device for surgical port closure includes a head portion having at least one suture guide inlet and at least one suture retainer, the head portion being configured to contact a suture knot inside an incision to close a portion of a surgical port made by the incision, and a coupling member operatively connected to the head portion, the coupling member enabling releasable connection of the knot pusher device to a suturing device.

14 Claims, 9 Drawing Sheets

SPECIALIZED KNOT PUSHER FOR SURGICAL PORT CLOSURE AND SUTURING DEVICES

CROSS-REFERENCE TO RELATED APPLICATIONS

This application claims the benefit of U.S. Provisional Application Ser. No. 62/828,680, filed on Apr. 3, 2019, which is hereby incorporated by reference herein in its entirety.

FIELD OF THE INVENTION

The present invention relates generally to surgical instruments and, more particularly, to an adaptable specialized knot pusher device, used in laparoscopy or robotic surgery.

BACKGROUND OF THE INVENTION

Laparoscopic surgery, also known as minimally invasive surgery, is a modern surgical technique that dramatically reduces the amount of pain, bleeding, scaring and recovery time associated with more typical open surgery. When performing laparoscopic surgery, the work site is typically accessible through small ports, cannulas or openings where elongated instruments are introduced into the body. When the procedure is completed the surgeon proceeds to close the surgical wound using suturing materials, whereby extracorporeal knots are created and leveraged corporeally. The formation and delivery of the knots to the desired site often requires the surgeon to develop new skills and dexterity. The procedure is often tedious and time-consuming.

Among the most advanced systems used today in laparoscopic surgery are the da Vinci Surgical System™. This system is a robotically assisted system that, through small openings, performs precise surgical procedures. It uses similar tools as in other types of laparoscopic surgeries but sometimes even smaller in size. This robotically assisted system permits surgeons to perform laparoscopic procedures without physically touching the patient, and in some cases without even being in the same room. Even in these advanced robotic procedures, however, there is a need to close the ports and deliver a knot.

Among the most common laparoscopic surgeries performed today are cholecystectomies. A cholecystectomy is a procedure whereby through laparoscopic surgery the gall bladder is removed. This procedure typically requires 4 incisions of 5-10 mm in diameter. Specialized, elongated tools such as graspers, scissors, suction irrigators and cauterizers are among those inserted through an opening to perform their functions. Due to improved patient outcomes such as reduced post-operative pain, quicker recovery times, minimal scaring, smaller incisions, reduced bleeding, reduced chances of infections and lower morbidity rates, the laparoscopic field has grown immensely compared to open surgery.

As alluded to above, the final step of the laparoscopic procedure is the closing of the incision using sutures and knots. As will be appreciated, it is critical that a closed surgical knot bind the suture materials together while also binding the tissue. Moreover, the knot must not slip, and must remain tight until the wound is healed. Failure to close laparoscopic ports correctly can result in several complications, including herniation, infection, and wound closure failure. Herniation is a dangerous complication that can result in up to 8% of cases, and can result in pain, discomfort, organ injury and even death. Hernias often require emergency surgery, and increase morbidity and health care costs.

In connection with the above, to properly close the laparoscopic ports, the fascia tissue layer must be sutured closed. This is the strongest layer, and it provides the strength necessary to hold the surgical opening closed. The fascia layer is the deepest layer of tissue, located at the bottom of the abdominal wall and just above the intra-abdominal cavity and organs. Closing this layer is challenging, since it is at the bottom of a deep small hole, which limits the surgeon's visibility, dexterity and reach.

Among the factors that affect proper closing are the thickness of the skin, the amount of fatty tissue, and muscle size below the top surface. These are some of the factors that determine how deep the surgical suture knot is to be placed. In obese patients, surgeons are finding it harder to properly close the patient's surgical incisions. In particular, even though in many cases, surgeons use their fingers to push a suture knot into the incision, they are limited by the length and thickness of their fingers, and are often not able to properly place it deep down in the correct position, particularly where a thick layer of fatty tissue makes it difficult to reach the facia layer where the knot must be placed. The failure to achieve this vital step can result in improper knot placement, weakened knot strength, over tightening of the tissue, and other problems ultimately resulting in the wound not healing properly and giving greater risk to infections and hernias.

In laparoscopic procedures when closing an open incision, it is necessary to insert suture knots deep into an open surgical wound so as to form a tight bind within the adjacent fascial skin layers. Surgeons have tried using just their fingers to push the suture knot into the correct position but due to a patient's thick abdominal wall, it's not always possible, especially in bariatric procedures where the patient is often obese. In these patients, it can be difficult or impossible to see the bottom of the incision, and a finger that is too short or too thick, will not be able to push the knot securely down.

While there exist in the field various knot pusher devices to assist a surgeon in pushing a suture knot to a proper location, such devices are typically separate tools that are cumbersome to use. In view of the above, there is a need for an improved knot pusher device that is specially designed for closing laparoscopic ports.

SUMMARY OF THE INVENTION

It is an object of the present invention to provide a specialized surgical tool for use in laparoscopic surgery.

It is another object of the present invention to provide a specialized knot pusher device for assisting in closing laparoscopic surgery ports.

It is another object of the present invention to provide a specialized knot pusher device to assist in knot placement during port closure.

It is another object of the present invention to provide a knot pusher device having novel features that provide superior knot pusher functionality when closing a laparoscopic port.

It is another object of the present invention to provide a specialized knot pusher device that can be used as a stand-alone device.

It is another object of the present invention to provide a specialized knot pusher device that can be selectively coupled to a suturing device to provide an accompanying knot pushing feature, to assist the surgeon in placing the suture knot correctly into the incision.

These and other objects are achieved by the present invention.

According to an embodiment of the present invention, a knot pusher device for surgical port closure includes a head portion having at least one suture guide inlet and at least one suture retainer, the head portion being configured to contact a suture knot inside an incision to close a portion of a surgical port made by the incision, and a coupling member operatively connected to the head portion, the coupling member enabling releasable connection of the knot pusher device to a suturing device.

According to another embodiment of the present invention, a method for suturing incisions through multiple layers of a body utilizing a knot pusher device for surgical port closure includes the steps of threading a suture thread having a first suture leg and a second suture leg though a lowest layer of the multiple layers of the body adjacent to an incision, crossing the first suture leg and the second suture leg, wrapping the first suture leg around the second suture leg, pulling upwards on at least one of the first suture leg and the second suture leg to form the suture knot, positioning the first suture leg and the second suture leg through at least one suture retainer in a head portion of a knot pusher device, pulling upward on the first suture leg and the second suture leg, and pushing the suture knot with the knot pusher device to a desired position inside the incision.

According to yet another embodiment of the present invention, a knot pusher device for surgical port closure includes an elongate shaft and a head portion connected to the elongate shaft, the head portion having at least one suture guide inlet and at least one suture retainer, the head portion being configured to contact a suture knot inside an incision to close a portion of a surgical port made by the incision.

BRIEF DESCRIPTION OF DRAWINGS

The present invention will be better understood from reading the following description of non-limiting embodiments, with reference to the attached drawings, wherein below.

DETAILED DESCRIPTION OF THE INVENTION

Figures 1A, 1B:
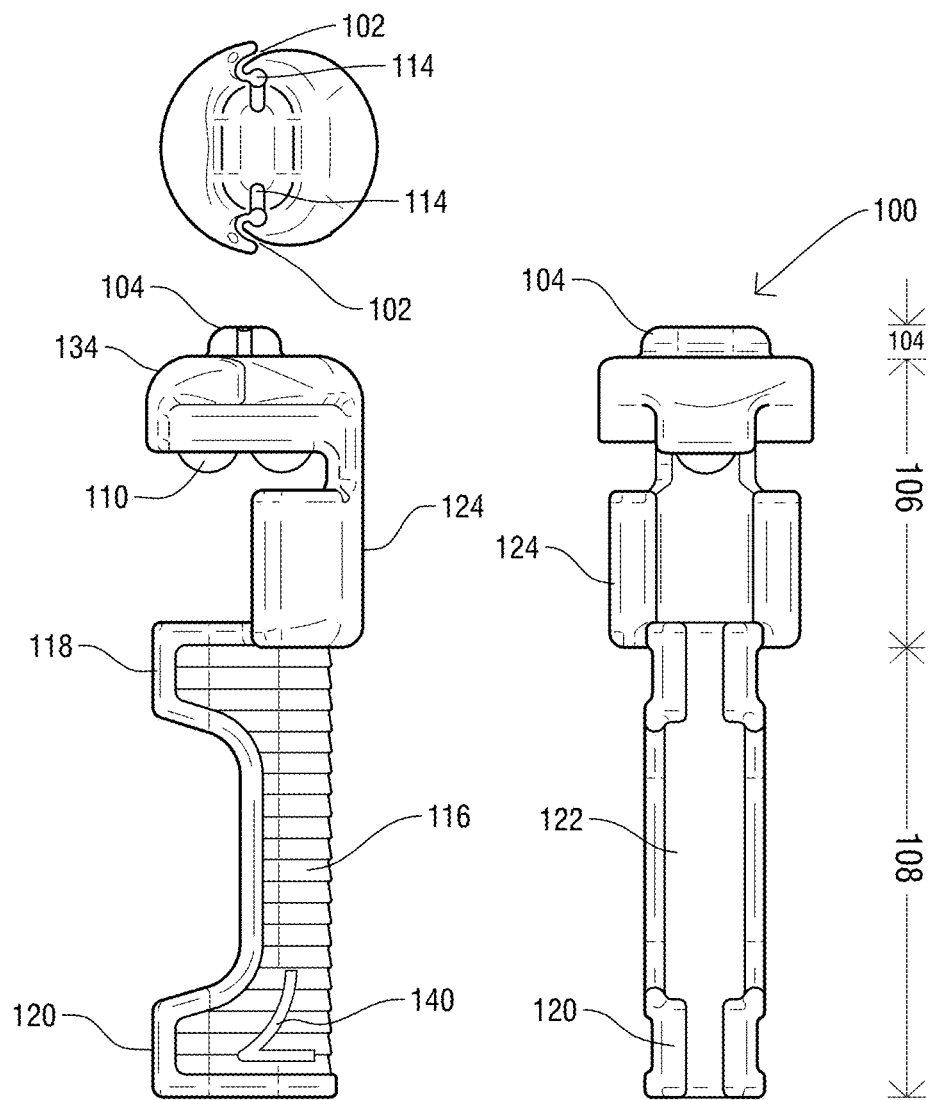
FIG. 1A is a side elevational view of a knot pusher device according to an embodiment of the present invention.
FIG. 1B is a front elevational view of the knot pusher device of FIG. 1A.

While the various features of this invention are hereinafter described and illustrated as being particularly adapted for providing rigidity to instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

Referring to FIGS. 1A-2B, a knot pusher device 100 according to an embodiment of the present invention is illustrated. As shown therein, the knot pusher device 100 includes a body portion 106, a head portion 104 unitarily formed with, or otherwise connected to, and extending from, the body portion 106, and a coupling member 108 unitarily formed with, or otherwise connected to the body portion 106 opposite the head portion 104. The coupling member 108 and the body portion 106 define therethrough a generally hollow passage for receiving the shaft of a suture closure device, as discussed hereinafter. As best shown in FIG. 2A, the passageway extends from an open, lower end of the coupling member 108 to the closed, upper end defined by the head portion 104. In addition, the coupling member 108 and the body portion 106 have a longitudinal slot that provides access to the hollow passageway from a lateral direction, enabling the suture closure device to be inserted into the hollow passageway through the slot. As further shown therein, a central axis 130 of the knot pusher device 100 passes through a contacting surface of the head portion 104.

Figures 2A, 2B:
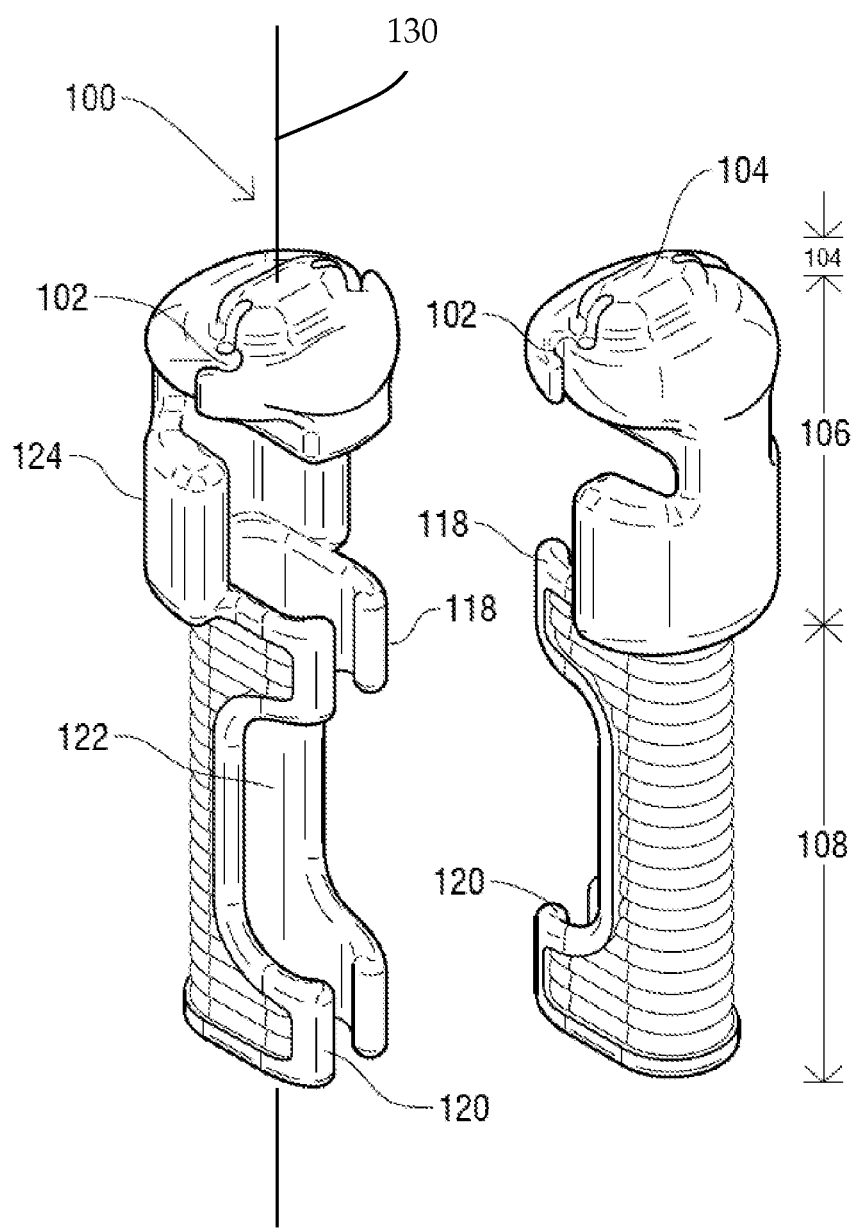
FIG. 2A is a perspective view of the knot pusher device of FIG. 1A.
FIG. 2B is another perspective view of the knot pusher device of FIG. 1A.

With particular reference to FIGS. 1A, 2A and 2B, the head portion 104 includes at least one suture guide inlet 102 and a suture retainer 114 in communication with the suture guide inlet 102. In an embodiment, the device 100 includes a pair of guide inlets 102 and retainers 114. The suture guide inlet 102 is configured and utilized to guide a suture into the suture retainer 114. In an embodiment, the head portion 104 having a curved or arcuate peripheral edge 134 that facilitates entry of the knot pusher device into a surgical opening and presents an atraumatic surface to the tissues of a patient, as discussed hereinafter.

Referring specifically to FIGS. 2A and 2B, the coupling member 108 includes a pair of resilient or deformable upper gripping arms 118 located on opposing sides of the longitudinal slot and adjacent to the body portion 106, and a pair of resilient or deformable lower gripping arms 120 located on opposing sides of the longitudinal slot adjacent to the lower end of the coupling member 108. The gripping arms 118, 120 are configured to help guide the knot pusher device 100 onto a suture closure device and to releasably couple the knot pusher device 100 to a suture device 101. The coupling member 108 also includes a recessed holding arm 122 that serves as the spine of the device 100, and receives the suture closure device. As will be appreciated, therefore, the coupling member 108 allows for. the releasable connection of the knot pusher device 100 to a suture closure device via a snap-fit like coupling.

Figure 4:
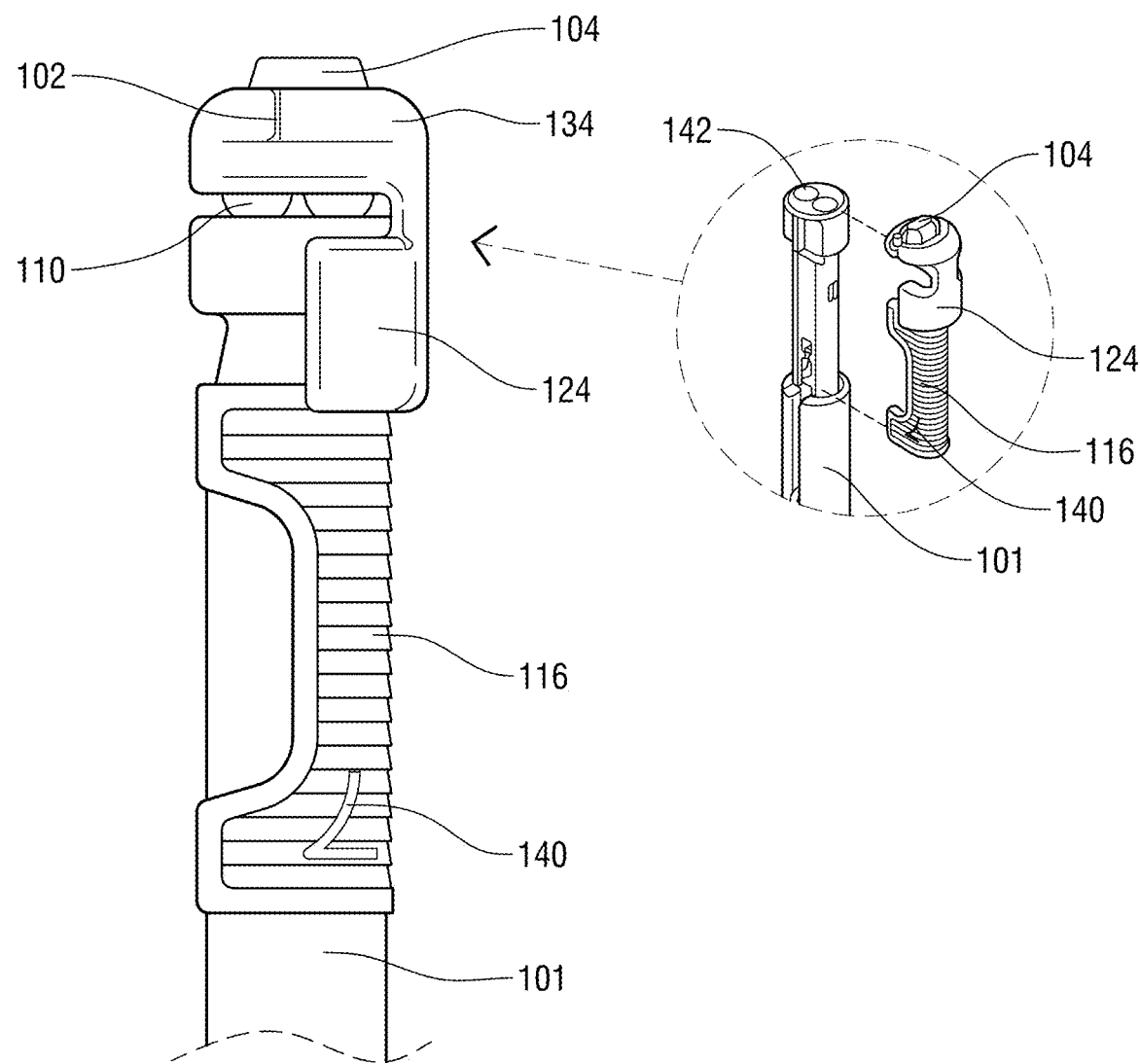
FIG. 4 presents is an enlarged, detail view showing the knot pusher device attached to the top of the suture closure device.

In an embodiment, the knot pusher device 100 may include two specialized circular passage blocking members 110 that may be used to seal off the liquid passage area of the suture closure device 101 when the knot pusher device is coupled to the suture closure device 101. As best shown in FIG. 4, the knot pusher device 100 may also include a plurality of gripping ribs 116 along the exterior of the device 100, which enables easy and secure handling and manipulation even when liquids and/or bodily fluids are present. A specialized suture holding member 140 may be formed on the exterior of the device 100, and is used to hold the suture in the proper orientation when forming the suture knot, as disclosed hereinafter.

Figures 3A, 3B:
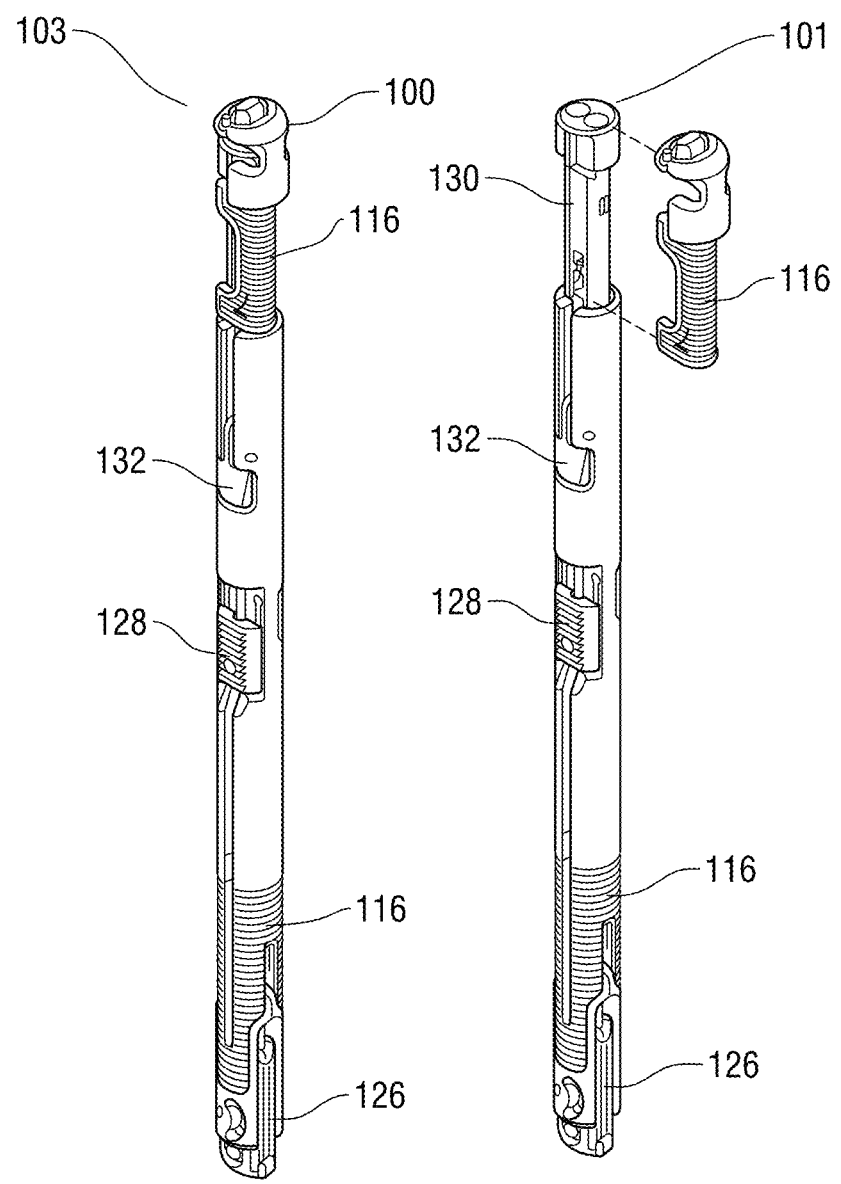
FIG. 3A is a perspective view of the knot pusher device of FIG. 1A attached to a suture closure device.
FIG. 3B is a perspective view illustrating the knot pusher device and suture closure device prior to the knot pusher device being attached to the suture closure device.

Turning now to FIGS. 3A and 3B, the manner in which the knot pusher device 100 is coupled to a suture closure device 101 is shown. As shown therein, the suture closure device 101 may include a plunger release latch 132 that may be used to cause the knot pusher device 100 to pop upwards and disengage a pair of needles (not show) used for administering an analgesic. A T-Bar orientation latch 128 is used to orient the T-Bar 126.

Turning now to FIG. 4, the knot pusher device 100 is shown coupled to the top of the suture closure device 101. As shown, suture direction holder 140 is used to guide the suture string from the suture guide inlet 102 and suture retainer 114. When coupled to the suture closure device, the blocking members 110 of the knot pusher device 100 are seated in the passages 142 of the suture closure device 101, sealing the openings of the passages 142 and preventing any liquid to enter or leave the suture closure device 101.

Figure 5:
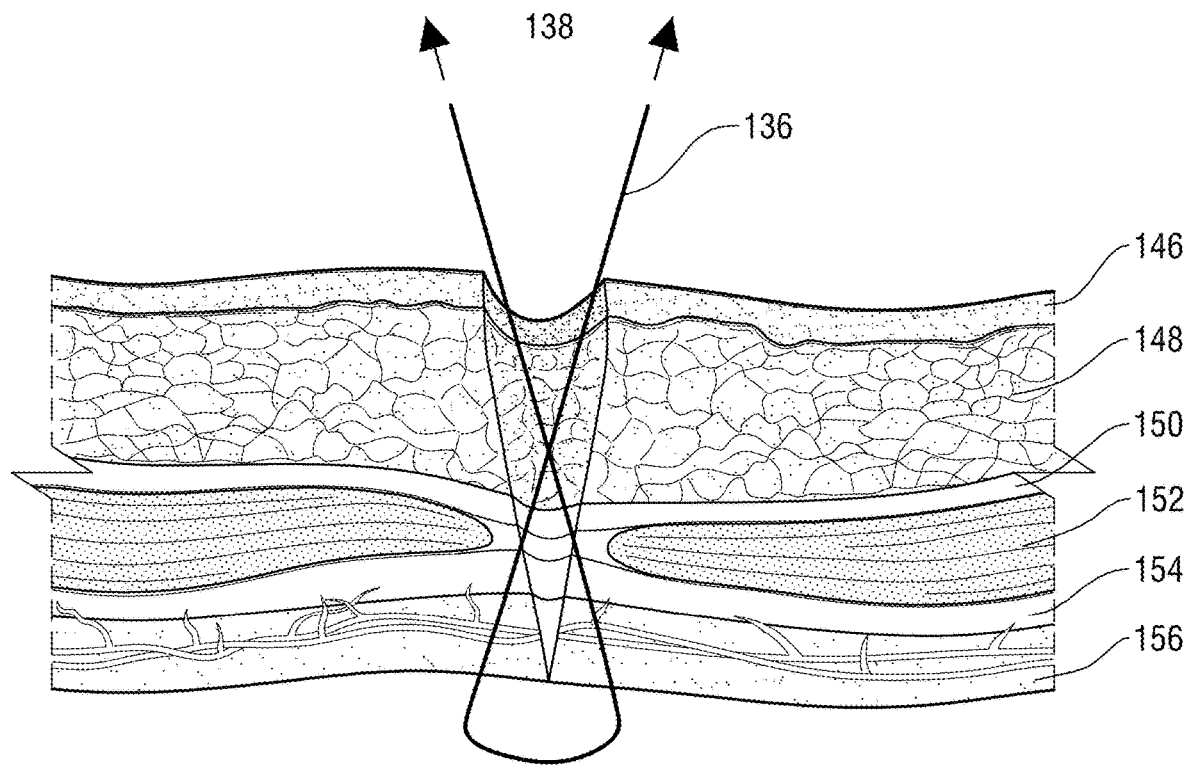
FIG. 5 is a cross-sectional view of the abdomen of a patient, illustrating a first step of a surgical knot process.

Turning now to FIGS. 5-8, use of the suture closure device 101 and knot pusher device 100 to close a surgical opening is shown. As shown in FIG. 5, suture 144 is depicted having an upward force 138 applied to it beginning the tightening process of the different skin layers which include the epidermis 146, followed downwards by the fatty tissue 148, the anterior rectus sheath 150, the rectus abdominis muscle 152, the rectus abdominis sheath 154 and, finally, the peritoneum 156.

Figure 6:
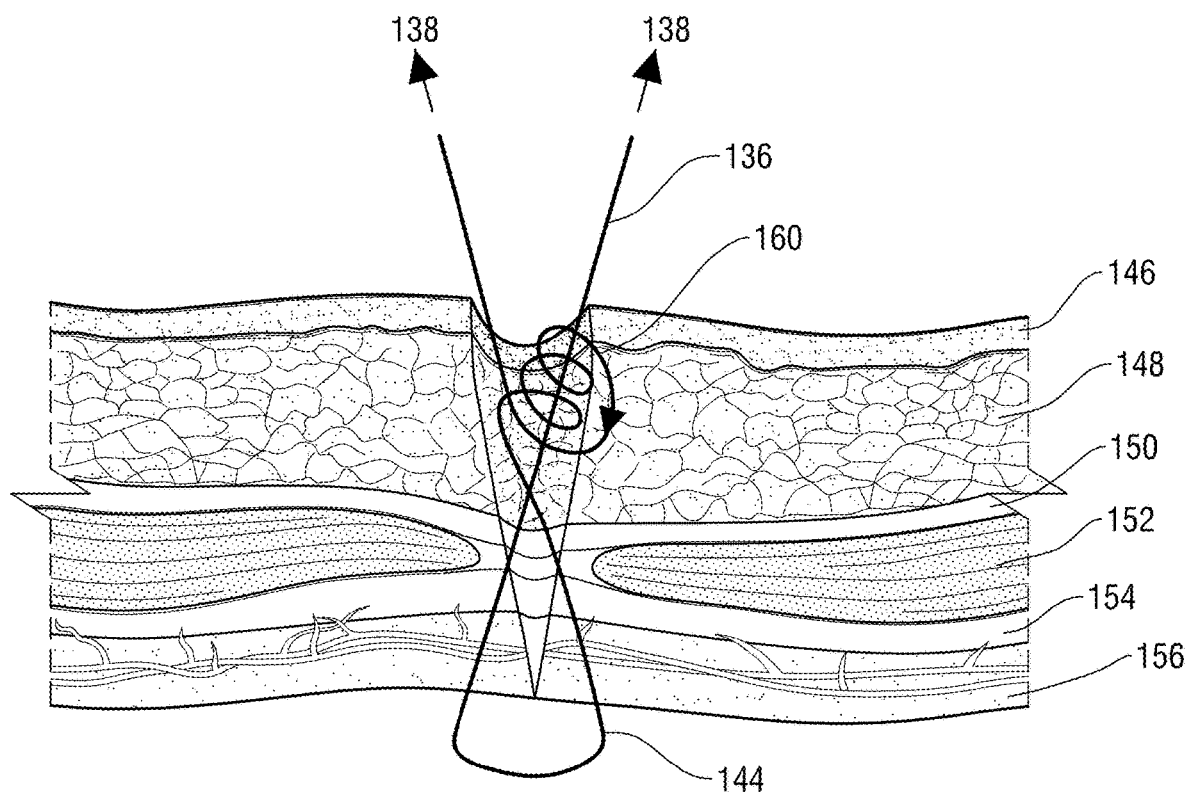
FIG. 6 is a cross-sectional view of the abdomen of a patient, illustrating the process of creating a knot.
Figure 7:
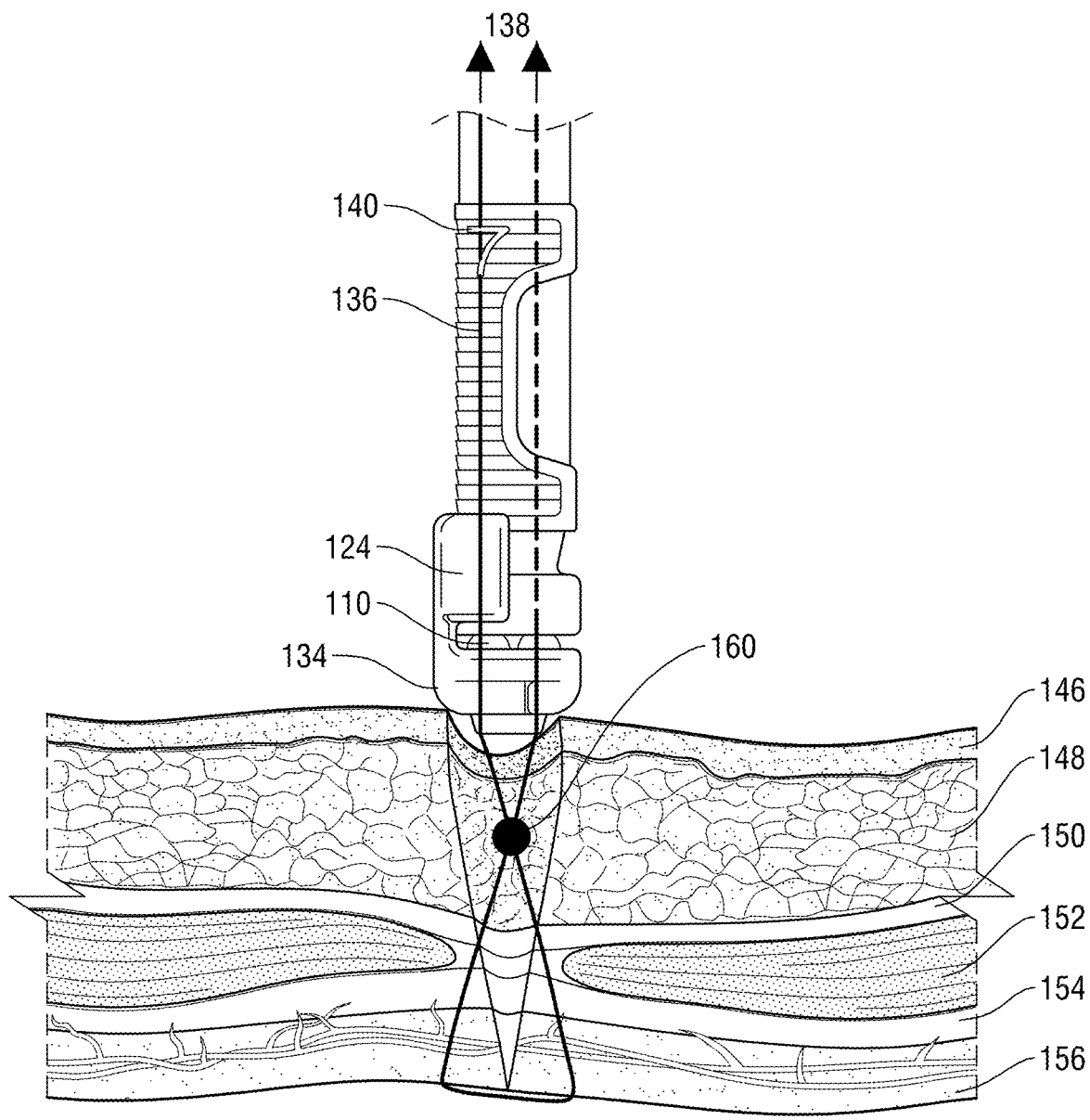
FIG. 7 is a cross-sectional view of the abdomen of a patient, illustrating positioning of the knot pusher device for pushing the knot into the suture.

FIG. 6 illustrates the subsequent step of creating a surgical knot by wrapping one of the legs of the suture 136, 144 around the opposite suture leg and pulling upwards to form the suture knot 160. As shown in FIG. 7, the suture closure device 100 and knot pusher device 100 are then utilized to tighten the knot 160. In particular, FIG. 7 shows the knot pusher device 100 properly oriented for tightening the surgical knot 160 and pushing the surgical knot 160, for tightening the different layers of the skin starting from the peritoneum 156, the posterior rectus sheath 154, the rectus muscle 152, the anterior rectus sheath 150, the fatty tissue layer 148, and epidermis area 146.

Figure 8:
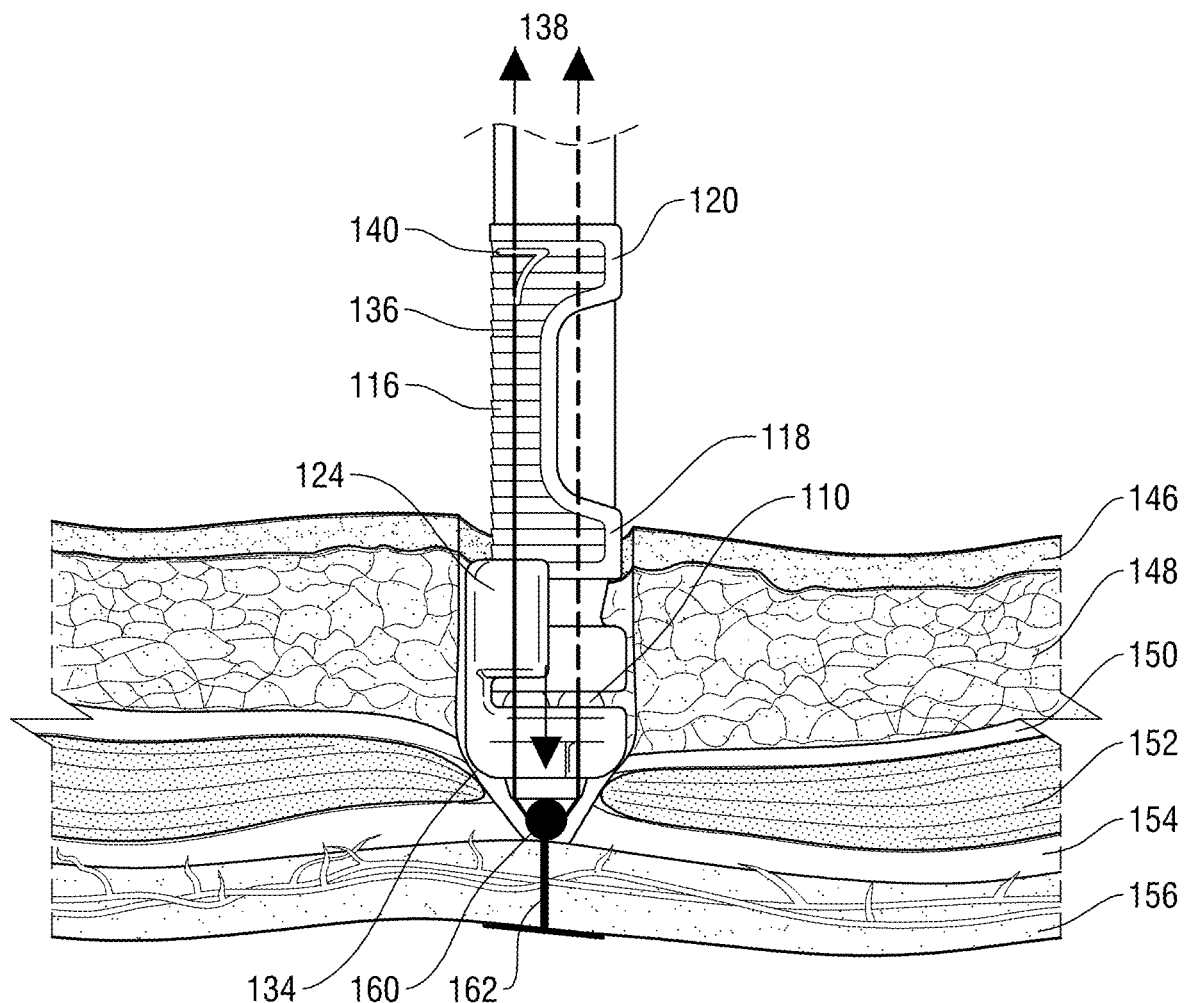
FIG. 8 is a cross-sectional view of the abdomen of a patient, illustrating use of the knot pusher device to correctly push the knot deep into the surgical opening.

With reference to FIG. 8, the knot pusher device 100 and closure device 101 are shown utilized to push the surgical knot 160 deep into the surgical opening. The surgical knot 160, the closed suture 162 and suture 136 apply forces in a "Y" type configuration providing the maximum outward pressure to the surgical knot 160 while still pushing down and better positioning the suture knot 160. Since the suture guide inlet 102 and suture direction holder 140 guide the suture through the top of the surgical opening, pressure is applied correctly to maximize the leverage of the suture knot 160.

As disclosed above, the present invention therefore provides a specialized knot pusher device that can be selectively coupled to a suturing/closure device to provide an accompanying knot pushing feature, to assist the surgeon in placing the suture knot correctly into the incision. That is, the present invention provides a knot pusher device and closure device that can be integrated or embedded into one tool.

Importantly, the curved/rounded head 104 permits the suture to flow smoothly as it enters the open wound. It pulls the suture legs directly outwards, to evenly form the knot, while still having a rounded edge that allows the suture legs to reorient vertically and be pulled smoothly from outside the laparoscopic incision. This tapered head also allows proper tightening of the suture when it reaches the distal end.

The suture guide inlets 102 and a suture retainers 114 additionally provide a novel means for securing the suture in its path with the security of a closed-end knot pusher while enjoying the benefits of an open-ended knot pusher. This allows the surgeon to quickly load the suture legs into the pathway without having to worry about them coming out and becoming loose while the knot is pushed distally into place.

As indicated above, there is no device or system currently available for laparoscopic surgeons with the proper length and diameter for closing the deep and narrow port sites of obese patients. Until now, surgeons have had to rely on their fingers to press the knot firmly onto the deepest layers, and this is not possible in many obese patients with abdominal walls two or three times deeper than an average finger length. The present invention obviates these issues.

Figures 9A, 9B:
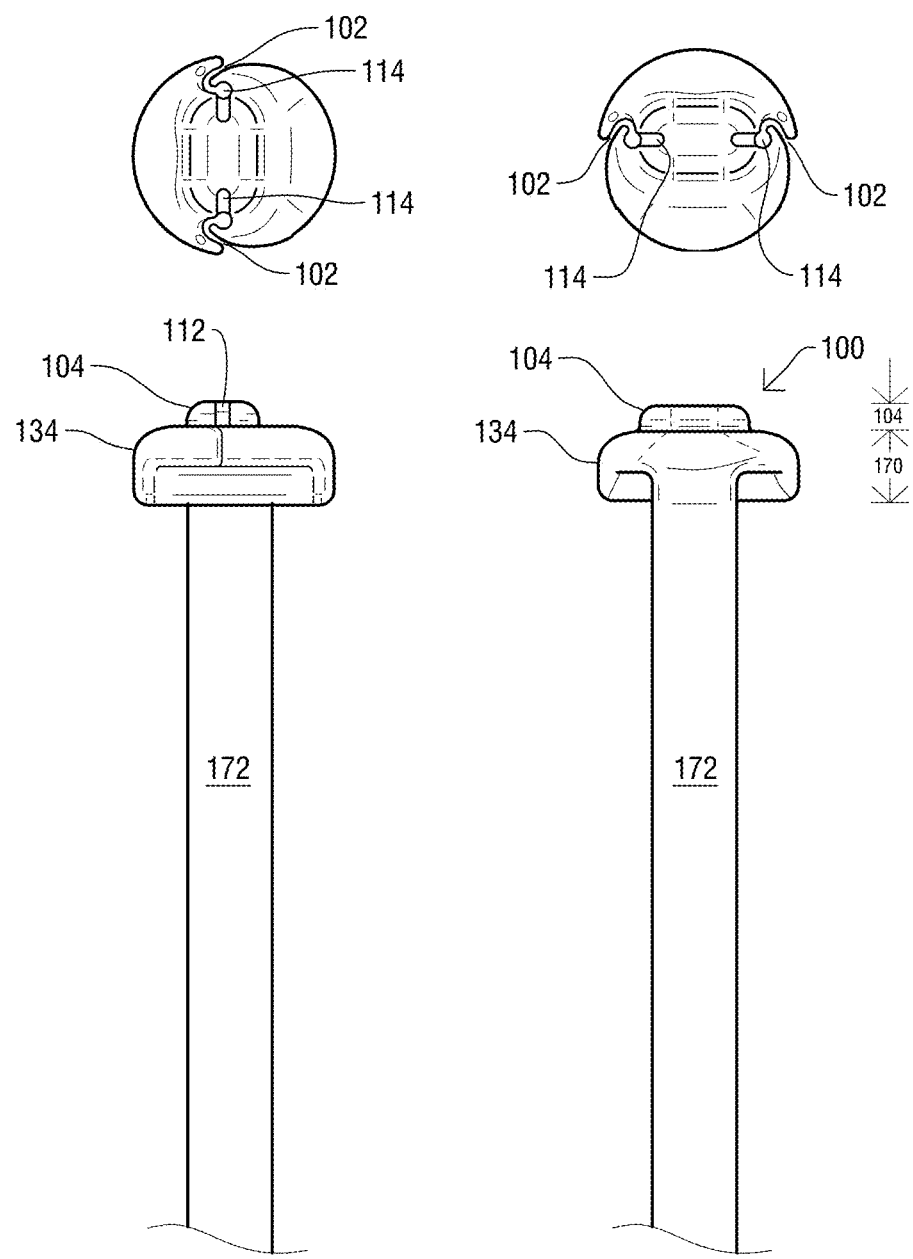
FIG. 9A is a side elevational view of a standalone knot pusher device according to another embodiment of the present invention.
FIG. 9B is a front elevational view of the standalone knot pusher device of FIG. 9A.

Turning finally to FIGS. 9A and 9B, a knot pusher device according to an alternative embodiment of the present invention is shown. As shown therein, the knot pusher device is designed to operate as a separate but compatible stand-alone device to a typical suturing/closure device. As illustrated, the knot pusher device includes a shaft 172 having a lower head portion 170 and an upper head portion 104 that is substantially similar in configuration to the head portion 104 of the knot pusher device disclosed above in connection with FIGS. 1A-8, where like reference numerals designate like parts. In an embodiment, the shaft 172 has a diameter and length compatible with laparoscopic ports. In an embodiment, the diameter of the shaft 172 is between about 5-10 mm to accommodate the typical trocar sizes, and the length of the shaft 172 is between about 10-20 cm to accommodate most abdominal wall thicknesses.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A knot pusher device for surgical port closure, comprising:
   a head portion having at least one suture guide inlet and at least one suture retainer in communication with the at least one suture guide inlet such that a suture can be inserted into the at least one suture retainer by passing through the at least one suture guide inlet, the at least one suture retainer forming at least one passage in a distal end of the head portion for permitting the suture to extend through the distal end, the head portion further including a distal end surface and a projection that protrudes from and extends above the distal end surface, the projection having a contacting surface adjacent to the at least one passage at the distal end, the contacting surface having a solid center portion and being configured to contact a suture knot inside an incision to close a portion of a surgical port made by the incision; and a coupling member operatively connected to the head portion, the coupling member enabling releasable connection of the knot pusher device to a suturing device;

wherein the contacting surface is located such that a central axis of the knot pusher device passes through the solid center portion of the contacting surface;

wherein the at least one suture guide inlet is a pair of suture guide inlets located on opposing sides of the distal end surface, and the at least one suture retainer is a pair of suture retainers located on opposing sides of the contacting surface; and wherein the contacting surface defines a continuous surface between the pair of suture retainers.

2. The knot pusher device of claim 1, further comprising:
a body portion connected to the head portion;
wherein the body portion is intermediate the head portion and the coupling member.

3. The knot pusher device of claim 1, wherein:
the coupling member defines a hollow passageway configured to receive the suturing device therein.

4. The knot pusher device of claim 3, wherein:
the coupling member includes a longitudinal slot providing access to the hollow passageway and a plurality of deformable gripping members configured to releasably retain the knot pusher device on the suturing device.

5. The knot pusher device of claim 4, wherein:
a first deformable gripping member of the plurality of gripping members is located on one side of the longitudinal slot; and
a second deformable gripping member of the plurality of gripping members is located on an opposing side of the longitudinal slot.

6. The knot pusher device of claim 1, wherein:
the head portion includes an atraumatic, curved peripheral surface.

7. The knot pusher device of claim 1, further comprising;
an array of gripping ribs on an exterior surface of the knot pusher device.

8. The knot pusher device of claim 1, further comprising:
at least one suture direction holder.

9. The knot pusher device of claim 1, wherein:
the coupling member has a longitudinal opening located on one side thereof for receiving the suturing device therethrough.

10. The knot pusher device of claim 1, further comprising:
at least one semi-spherical blocking member configured to seal off a liquid passage area of the suturing device when the knot pusher device is connected to the suturing device.

11. A knot pusher device for surgical port closure, comprising:
a head portion having at least one suture guide inlet and at least one suture retainer in communication with the at least one suture guide inlet such that a suture can be inserted into the at least one suture retainer by passing through the at least one suture guide inlet, the at least one suture retainer forming at least one passage in a distal end of the head portion for permitting the suture to extend through the distal end, the head portion further including a contacting surface adjacent to the at least one passage at the distal end, the contacting surface having a solid center portion and being configured to contact a suture knot inside an incision to close a portion of a surgical port made by the incision; and a coupling member operatively connected to the head portion, the coupling member enabling releasable connection of the knot pusher device to a suturing device;

wherein the contacting surface is located such that a central axis of the knot pusher device passes through the solid center portion of the contacting surface;

wherein the at least one suture guide inlet is a pair of suture guide inlets located on opposing sides of the contacting surface, and the at least one suture retainer is a pair of suture retainers located on opposing sides of the contacting surface;

wherein the contacting surface defines a continuous surface between the pair of suture retainers;

wherein the coupling member defines a hollow passageway configured to receive the suturing device therein;

wherein the coupling member includes a longitudinal slot providing access to the hollow passageway and a plurality of deformable gripping members configured to releasably retain the knot pusher device on the suturing device; and wherein the plurality of deformable gripping members include an upper pair of gripping members and a lower pair of gripping members spaced from the upper pair of gripping members.

12. A knot pusher device for surgical port closure, comprising:
an elongate shaft; and
a head portion connected to the elongate shaft, the head portion having a pair of suture guide inlets and a corresponding pair of suture retainers, the pair of suture retainers forming at least one passage in a distal end of the head portion for permitting a suture to extend through the distal end, the head portion having a distal end surface and a projection that protrudes from and extends above the distal end surface, the projection having a contacting surface adjacent to the at least one passage at the distal end and being configured to contact a suture knot inside an incision to close a portion of a surgical port made by the incision;

wherein the pair of suture guide inlets are located on opposing sides of the distal end surface;

wherein the pair of suture retainers are located on opposing sides of the contacting surface; and wherein the contacting surface has a solid center portion defining a continuous surface between the pair of suture retainers;

wherein a largest dimension of the contacting surface is less than a diameter of the head portion.

13. The knot pusher device of claim 12, wherein:
the elongated shaft has a length between about 10 cm and about 20 cm, and a diameter between about 5 mm and about 10 mm.

14. A knot pusher device for surgical port closure, comprising:
a head portion having a pair of suture guide inlets and one a corresponding pair of suture retainers, the pair of suture retainers forming at least one passage in a distal end of the head portion for permitting a suture to extend through the distal end, the head portion further including a distal end surface and a projection that protrudes from and extends above the distal end surface, the projection having a contacting surface adjacent to the at least one passage at the distal end and being configured to contact a suture knot inside an incision to close a portion of a surgical port made by the incision; and a coupling member operatively connected to the head portion, the coupling member enabling releasable connection of the knot pusher device to a suturing device;

wherein the pair of suture guide inlets are located on opposing sides of the distal end surface;

wherein the pair of suture retainers are located on opposing sides of the contacting surface; and wherein the contacting surface has a solid center portion defining a continuous surface between the pair of suture retainers.

\* \* \* \* \*